US010820854B2

(12) United States Patent
Luo

(10) Patent No.: US 10,820,854 B2
(45) Date of Patent: Nov. 3, 2020

(54) ELECTRONIC SNORE-CEASING DEVICE AND METHOD FOR SNORE-CEASING

(71) Applicant: Shenzhen VVFLY Electronics Co., Ltd., Shenzhen (CN)

(72) Inventor: Qiang Luo, Shenzhen (CN)

(73) Assignee: SHENZHEN VVFLY ELECTRONICS CO. LTD., Guangdong (CN)

( * ) Notice: Subject to any disclaimer, the term of this patent is extended or adjusted under 35 U.S.C. 154(b) by 1128 days.

(21) Appl. No.: 15/033,971

(22) PCT Filed: Nov. 19, 2014

(86) PCT No.: PCT/CN2014/091648
§ 371 (c)(1),
(2) Date: May 3, 2016

(87) PCT Pub. No.: WO2015/074563
PCT Pub. Date: May 28, 2015

(65) Prior Publication Data
US 2016/0270720 A1    Sep. 22, 2016

(30) Foreign Application Priority Data

Nov. 22, 2013  (CN) .......................... 2013 1 0592276

(51) Int. Cl.
| A61H 23/00 | (2006.01) |
| A61B 5/00 | (2006.01) |
| A61B 7/00 | (2006.01) |
| A61N 1/36 | (2006.01) |
| A61F 5/56 | (2006.01) |
| A61B 7/04 | (2006.01) |

(52) U.S. Cl.
CPC .......... *A61B 5/4818* (2013.01); *A61B 5/6817* (2013.01); *A61B 5/725* (2013.01);
(Continued)

(58) Field of Classification Search
CPC ..... A61B 5/4818; A61B 5/6817; A61B 5/725; A61B 5/7282; A61B 5/746; A61B 7/003;
(Continued)

(56) References Cited

U.S. PATENT DOCUMENTS 4,644,330 A * 2/1987 Dowling .................. A61F 5/56
340/575
4,788,533 A * 11/1988 Mequignon ............... A61F 5/56
340/575
(Continued)

FOREIGN PATENT DOCUMENTS

| CN | 101340869 | 1/2009 |
| CN | 101351152 | 1/2009 |

(Continued)

OTHER PUBLICATIONS

International Search Report of PCT/CN2014/091648, dated Feb. 17, 2015, total 4 pages.

*Primary Examiner* — Tu A Vo
(74) *Attorney, Agent, or Firm* — Hamre, Schumann, Mueller & Larson, P.C.

(57) ABSTRACT

An electronic snore-ceasing device including an electroic snore-ceasing device body and a working module, the electronic snore-ceasing device body includes an ear-hook and an ear plug jointed together with the ear-hook, the working module is located inside the ear-hook and the ear plug; the working module includes a snore collecting circuit, a control circuit taking a Micro Control Unit (MCU) as a core thereof, a warning circuit, and a power supply circuit (24); when the control circuit determines that a received sound signal and vibration signal reach their respective threshold values, the control circuit transmits a control signal to the warning circuit located inside the ear plug, thereby activating the warning circuit to generate a sound stimulation signal, a (Continued)

vibration stimulation signal or an electrode stimulation signal that does not wake the user up in sleep to suppress snores.

12 Claims, 9 Drawing Sheets

(52) U.S. Cl.
CPC ............ *A61B 5/7282* (2013.01); *A61B 5/746* (2013.01); *A61B 7/003* (2013.01); *A61B 7/04* (2013.01); *A61F 5/56* (2013.01); *A61H 23/00* (2013.01); *A61N 1/3601* (2013.01); *A61B 2560/0475* (2013.01); *A61H 2201/10* (2013.01); *A61H 2230/405* (2013.01)

(58) Field of Classification Search
CPC ..... A61B 7/04; A61B 2560/0475; A61F 5/56; A61H 23/00; A61H 2201/10; A61H 2230/405; A61H 21/00; A61H 2023/002; A61H 23/004; A61H 23/006; A61H 23/02; A61H 2023/0209; A61N 1/3601; A61M 21/00; A61M 21/02; A61M 2021/0088; A61M 2021/0027
See application file for complete search history.

(56) References Cited

U.S. PATENT DOCUMENTS

| | | | | |
|---|---|---|---|---|
| 5,477,867 A | * | 12/1995 | Balkanyi | A61F 5/56 |
| | | | | 128/848 |
| 8,628,478 B2 | * | 1/2014 | Wolfe | A61B 5/024 |
| | | | | 600/509 |
| 2003/0199945 A1 | * | 10/2003 | Ciulla | A61F 5/56 |
| | | | | 607/48 |
| 2005/0065560 A1 | * | 3/2005 | Lee | A61B 5/113 |
| | | | | 607/6 |
| 2005/0211247 A1 | * | 9/2005 | Noda | A61B 5/6892 |
| | | | | 128/204.23 |
| 2007/0239225 A1 | * | 10/2007 | Saringer | A61F 5/56 |
| | | | | 607/42 |
| 2009/0293886 A1 | * | 12/2009 | Dedrick | A61F 5/56 |
| | | | | 128/848 |
| 2010/0228315 A1 | * | 9/2010 | Nielsen | A61B 5/0215 |
| | | | | 607/42 |
| 2010/0240945 A1 | * | 9/2010 | Bikko | A61B 5/02405 |
| | | | | 600/28 |
| 2012/0212345 A1 | * | 8/2012 | Harman | A61B 5/4818 |
| | | | | 340/575 |
| 2013/0204314 A1 | * | 8/2013 | Miller, III | A61N 1/3601 |
| | | | | 607/42 |
| 2014/0276227 A1 | * | 9/2014 | Perez | A61B 5/4818 |
| | | | | 600/586 |

FOREIGN PATENT DOCUMENTS

| | | |
|---|---|---|
| CN | 101785721 | 7/2010 |
| CN | 202568578 | 12/2012 |
| CN | 202619947 | 12/2012 |
| CN | 203710215 | 7/2014 |
| DE | 3322571 | 4/1984 |
| EP | 2281533 | 2/2011 |

* cited by examiner

ELECTRONIC SNORE-CEASING DEVICE AND METHOD FOR SNORE-CEASING

TECHNICAL FIELD

The present application relates to apparatuses for preventing snores from generating, and more particularly, relates to an electronic snore-ceasing device and a method for snore-ceasing used on ears.

BACKGROUND

Thirty percent or above of time of a human being is spent in sleep, whether a sleep quality of a person is good or bad directly affects the person's spirit and body health. Lots of people snore in sleep, which not only affects his/her sleep quality, but also affects other person's rest. In order to solve the pain of persons who snore in sleep and prevent various physiological and psychological illnesses caused by snoring, mechanical snore-ceasing devices and electronic snore-ceasing devices have been developed for stopping persons from snoring in sleep. The electronic snore-ceasing devices in the prior art, for example, a Chinese utility model patent (Patent No.: ZL 201220290555.0) with the title of "Intelligent snore-ceasing device" discloses an electronic snore-ceasing device, the electronic snore-ceasing device is worn on a user's wrist for detecting sounds made by the user in sleep. When it is detected that a snore of the user reaches a predetermined sound intensity, the snore-ceasing device at the wrist of the user sends a pulse signal, the pulse signal is transmitted to the central nervous of the user through an arm of the user and stimulates the user, so that the user can change his/her sleep gestures under the condition of not being waked up, thereby achieving an effect of suppressing and reducing snores. However, the snore-ceasing device is worn on the wrist of the user, and is far from a mouth and a nosal cavity of the user, and the position of the user's hand is very likely to be changed when the person is in sleep; therefore, when the hand is placed in a quilt, the snore-ceasing device may not be able to collect snores. It is obvious that this type of snore-ceasing device is far away from the position where the snores are sent and may collect much external acoustic noise, and thus an erroneous judgment is prone to be made; furthermore, the pulse stimulation signal sent from the electronic snore-ceasing device needs to be transmitted to the central nervous of the user through the arm of the user, it is obvious that an effect of the method of stimulating the arm of the user via electric current to adjust his/her breathing is unsatisfactory. In addition, the electronic snore-ceasing device worn on the arm of the user in the prior art fails to detect the snore-ceasing effect for the patient in real-time, such that a long-acting feedback mechanism can't be established.

BRIEF SUMMARY

A technical problem to be solved by the present application is to avoid aforesaid deficiencies of the prior art and provide an electronic snore-ceasing device and snore-ceasing method, thereby solving the problems that a snore-ceasing device in the prior art cannot judge snore accurately and the snore-ceasing effect thereof is unobvious.

The present application by provides such a technical solution to solve the aforesaid technical problems: providing an electronic snore-ceasing device, which comprises a snore-ceasing device body and a working module received in the snore-ceasing device body (1); in particular, the body comprises an ear-hook that is suitable to be hung on an auricle of a user, and an ear plug that is suitable to be placed inside an earhole of the user, the ear-hook and the ear plug are jointed together; the working module is placed inside an inner cavity formed by the ear-hook and the ear plug; the working module comprises a snore collecting circuit, a control circuit with a MCU as a core thereof, a warning circuit, and a power supply circuit; the snore collecting circuit and the warning circuit are respectively electrically connected to the control circuit, the power supply circuit provides low-voltage direct current electric power for the snore-ceasing circuit, the control circuit and the warning circuit respectively; the snore collecting circuit processes a sound signal and a head vibration signal generated by the user in sleep and collected by a microphone and a vibration sensor thereof, and transmits the processed sound signal and the vibration signal to the control circuit respectively; when the control circuit judges that the received sound signal and the vibration signal reach their respective threshold values, the control circuit sends a control signal to the warning circuit positioned inside the ear plug, such that the warning circuit is controlled to generate a sound stimulation signal or a vibration stimulation signal or an electrode stimulation signal that does not wake the user up to suppress snores.

Preferably, the electronic snore-ceasing device further comprises a snore collecting tube, one end of the snore collecting tube is connected to the ear plug, and the other end of the snore collecting pipeline is directed to a mouth and/or a nose of the user, the microphone is positioned inside the snore collecting tube.

The snore collecting circuit comprises a sound collecting circuit taking the microphone as a core thereof, and a vibration collecting circuit taking the vibration sensor as a core thereof; the sound collecting circuit comprises a first low-frequency filter circuit, a second low-frequency filter circuit and a first calculating and amplifying circuit; the microphone is configured for transforming a collected sound signal into an electric signal, wherein the electric signal to the first low-frequency filter circuit to be filtered, then the filtered electric signal is transmitted to the first calculating and amplifying circuit to be amplified, the amplified electric signal is transmitted to the second low-frequency filter circuit to be further filtered, and finally the further filtered electronic signal is transmitted to the control circuit; the vibration sensor is a triaxial accelerated speed sensor integrated circuit U12, the triaxial accelerated speed sensor integrated circuit U12 of the vibration collecting circuit transforms sensed vibration signals into the electric signals and transmits the electric signals to the control circuit.

The warning circuit comprises a sound stimulating circuit, a vibration stimulating circuit and an electrode stimulating circuit, the sound stimulating circuit, the vibration stimulating circuit and the electrode stimulating circuit are respectively electrically connected to the control circuit; the control circuit outputs a pulse signal, which activates a loudspeaker BL1 of the sound stimulating circuit to generate a sound stimulation signal, or activates a vibration electric motor T1 of the vibration stimulating circuit to generate a vibration signal, or activates an electric shock piece P1 of the electric stimulating circuit to generate an electrode stimulation signal.

The sound collecting circuit further comprises a second calculating and amplifying circuit, the electric signal further filtered by the second low-frequency filter circuit is not only transmitted to the control circuit but also transmitted to the second calculating and amplifying circuit to be further amplified, and the further amplified electric signal is transmitted to the control circuit.

The present application further provides another technical solution to solve the aforesaid technical problems: providing a snore-ceasing method using an electric snore-ceasing device, wherein the electric snore-ceasing device comprises an electric snore-ceasing device body and a working module received in the snore-ceasing device body (1), the electric snore-ceasing device body comprises an ear-hook that is suitable to be hung on an auricle of a user, and an ear plug that is suitable to be placed inside an earhole of the user; the snore-ceasing method comprises:

step A. using the working module to collect sounds and head vibrations generated by the user in sleep;

step B. when the working module judges that a collected sound is greater than or equal to a sound threshold value, and a collected vibration is greater than or equal to a vibration threshold value, generating one of a signal stimulation signal mode, a vibration stimulation signal mode, and an electrode stimulation signal mode that does not wake the user up and stimulates the user through the ear plug;

step C. using the working module to collecting the sounds and the head vibrations generated by the user in sleep again, when it is judged that a collected sound signal is still greater than or equal to the sound threshold value, and a collected vibration signal still reaches the vibration threshold value, enhancing an intensity of the original stimulation signal mode, or switching to another stimulation signal mode; when it is judged that the collected sound signal is smaller than the preset sound threshold value, or the collected vibration signal is less than the vibration threshold value, returning back to the step A.

The method further comprises: when the working module determines that the collected sound is greater than or equal to the sound threshold value, and the collected vibration is greater than or equal to the vibration threshold value, recording the number of the snore, snore data and/or vibration data for one time.

The method further comprises: when the working module determines that the collected sound is smaller than the sound threshold value, or the collected vibration is smaller than the vibration threshold value, recording the number of the snore-ceasing operation for one time.

The sound threshold value is set as sounds with the volume of 60 dB or more occurring for three or more times in one minute, or set as an experience value obtained by pre-recording and analyzing the user's snores.

The working module comprises a snore collecting circuit, a control circuit with a MCU as a core thereof, a warning circuit, and a power supply circuit; the snore collecting circuit and the warning circuit are respectively electrically connected to the control circuit, the power supply circuit provides electric power for the snore-ceasing circuit, the control circuit and the warning circuit respectively; the snore collecting circuit collects sounds and head vibrations generated by the user in sleep by using a microphone and a vibration sensor thereof.

The method further comprises setting a snore collecting tube, one end of the snore collecting tube is communicated with an ear plug, the other end of the snore collecting tube is directed to a mouth and/or a nose of the user, the microphone of the working module is placed inside the snore collecting tube to collecting the sounds generated by the user in sleep in a close proximity.

The snore collecting circuit comprises a sound collecting circuit with the microphone as a core thereof, and a vibration collecting circuit with the vibration sensor as a core thereof; the sound collecting circuit comprises a first low-frequency filter circuit, a second low-frequency filter circuit and a first calculating and amplifying circuit; by using the microphone, transforming a collected sound signal into an electric signal, and transmitting the electric signal to the first low-frequency filter circuit to be filtered, and then transmitting the filtered electric signal to the first calculating and amplifying circuit to be amplified, and transmitting the amplified electric signal to the second low-frequency filter circuit to be further filtered, and transmitting the further filtered electric signal to the control circuit; the vibration sensor is a triaxial accelerated speed sensor integrated circuit U12, by using the triaxial accelerated speed sensor integrated circuit U12 of the vibration collecting circuit, the sensed vibration signal is transformed into the electric signal and the electric signal is transmitted to the control circuit.

Compared with prior art, the advantageous effects of the present application is as follows: snores of the patient is detected in real-time through a low power consumption electronic circuit with a type of an electronic ear plug, since a snore collection position is quite close to a mouth and/or a nose of a patient, both snores of the patient and head vibrations caused by snoring can be collected very accurately, an interference by environmental sounds can be reduced effectively, thereby providing accurate references for accurately analyzing and judging snores; various interference signals are applied to the patient so as to stimulate the sleep process of the patient, and a stimulation effect can be monitored in real-time, so that a snore-ceasing effect can be achieved, and the patient can get high sleep quality.

DETAILED DESCRIPTION OF THE PREFERRED EMBODIMENT

The present application will be further described in detail hereafter with reference to preferred embodiments shown in the accompanying drawings.

Figure 1:
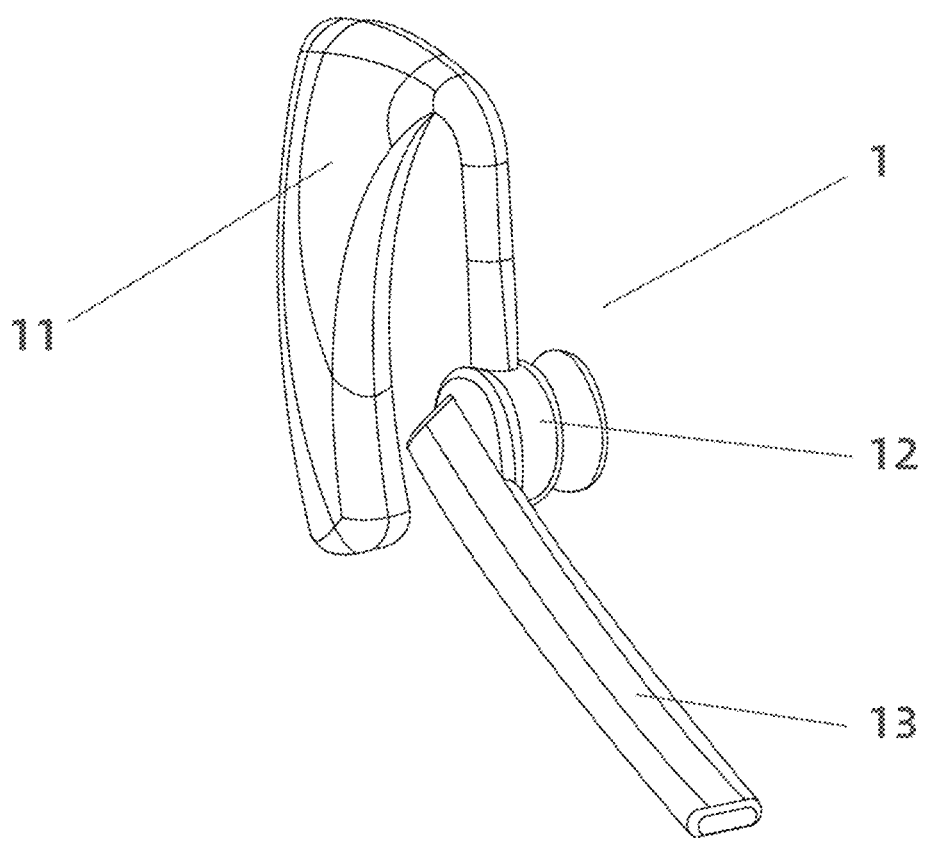
FIG. 1 illustrates an axonometric projection schematic view of an electronic snore-ceasing device in a preferred embodiment of an electronic snore-ceasing device and snore-ceasing method provided by the present application.
Figure 2:
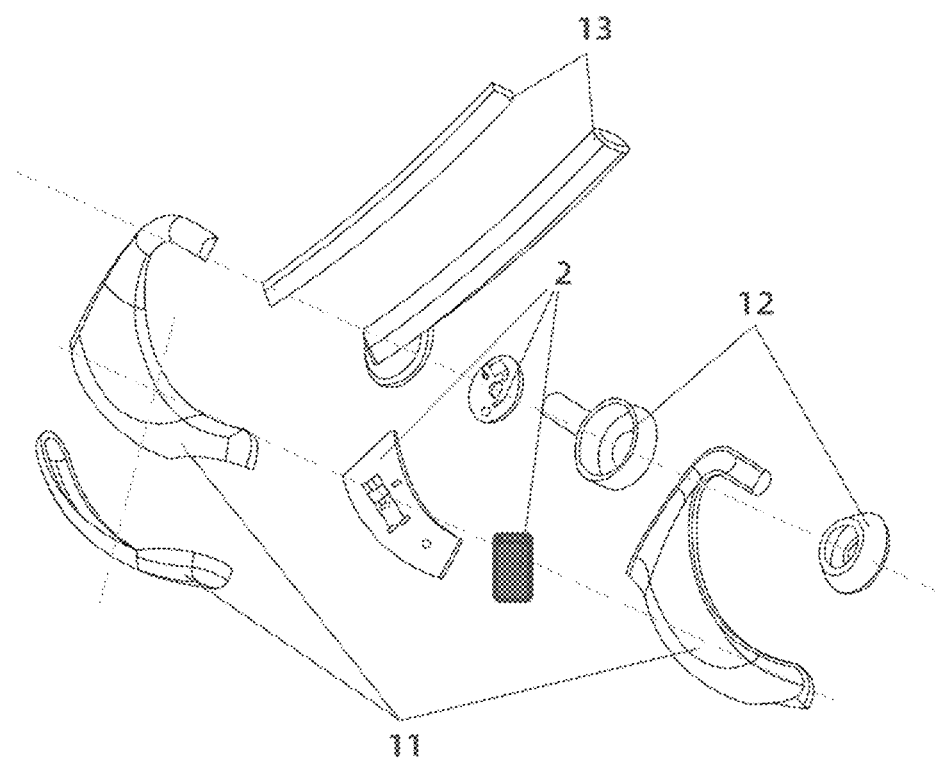
FIG. 2 illustrates an axonometric projection schematic view of a disassembled state of the components of the electronic snore-ceasing device of the preferred embodiment.
Figure 3:
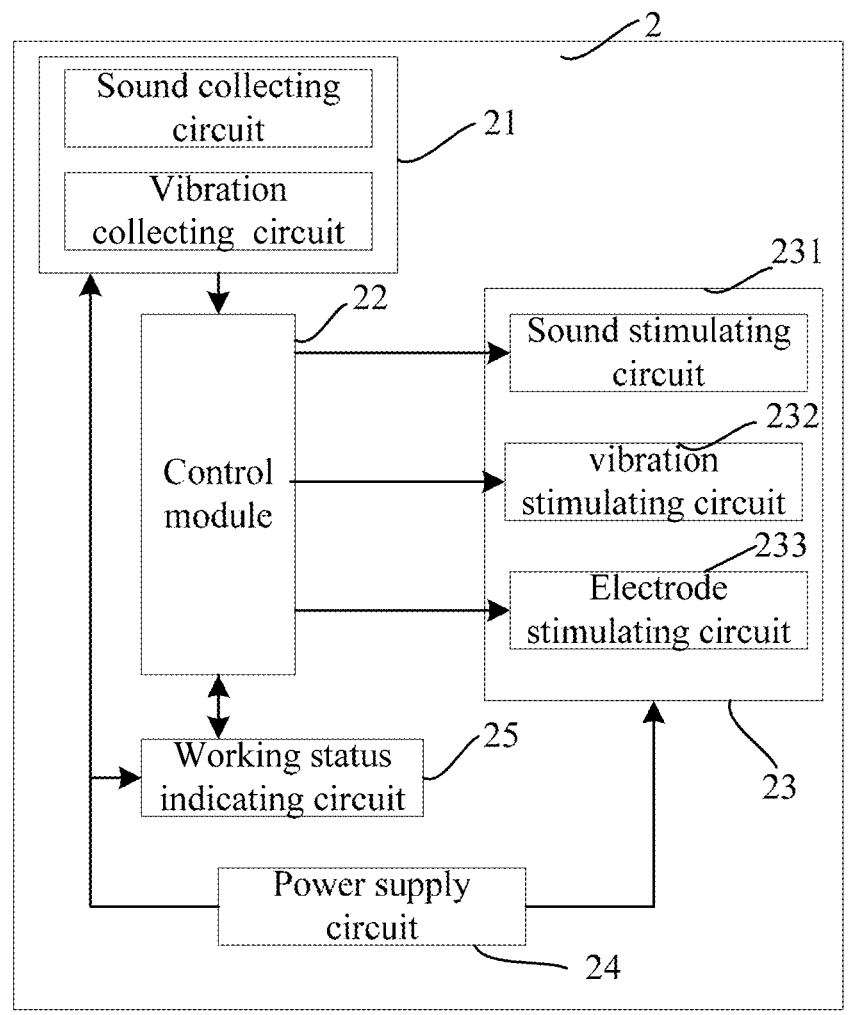
FIG. 3 illustrates a block diagram of the working module 2 of the electronic snore-ceasing device of the preferred embodiment.

Please refer to FIGS. 1-3, a preferred embodiment of the present application is an electronic snore-ceasing device, which comprises a snore-ceasing device body 1 and a working module 2 received in the snore-ceasing device body 1, the body 1 comprises an ear-hook 11 that is suitable to be hung on an auricle of a user, and an ear plug 12 that is suitable to be placed inside an earhole of the user, the ear-hook 11 and the ear plug 12 are jointed together; the working module 2 is arranged inside an inner cavity formed by the ear-hook 11 and the ear plug 12. Please refer to FIG. 3, the working module comprises a snore collecting circuit 21, a control circuit 22 taking a MCU (Micro Control Unit) as the core thereof, a warning circuit 23 and a power supply circuit 24; the snore collecting circuit 21 and the warning circuit 23 are respectively electrically connected to the control circuit 22, the power supply circuit 24 supplies the snore collecting circuit 21, the control circuit 22 and the warning circuit 23 with low-voltage direct current electric power respectively; the snore collecting circuit 21 processes a sound signal and a head vibration signal generated by the user in sleep and collected by a microphone and a vibration sensor thereof, and transmits the processed sound signal and vibration signal to the control circuit 22 respectively; when the control circuit 22 judges that the received sound signal and the head vibration signal reach their respective threshold values, the control circuit 22 sends a control signal to the warning circuit 23 positioned inside the ear plug 12, such that the warning circuit 23 is controlled to generate a sound stimulation signal, a vibration stimulation signal or an electrode stimulation signal that does not wake the user in sleep up, thereby suppressing snores.

Please refer to FIG. 2, in this embodiment, the body 1 is further provided with a snore collecting tube 13, one end of the snore collecting tube 13 is communicated with the ear plug 12, the other end of the snore collecting tube 13 is directed to a mouth and/or a nose of the user, and the microphone of the snore collecting tube 21 is positioned inside the snore collecting tube 13. In this way, snores generated by the user in sleep can be collected in a close distance and accurately.

Figure 4A:
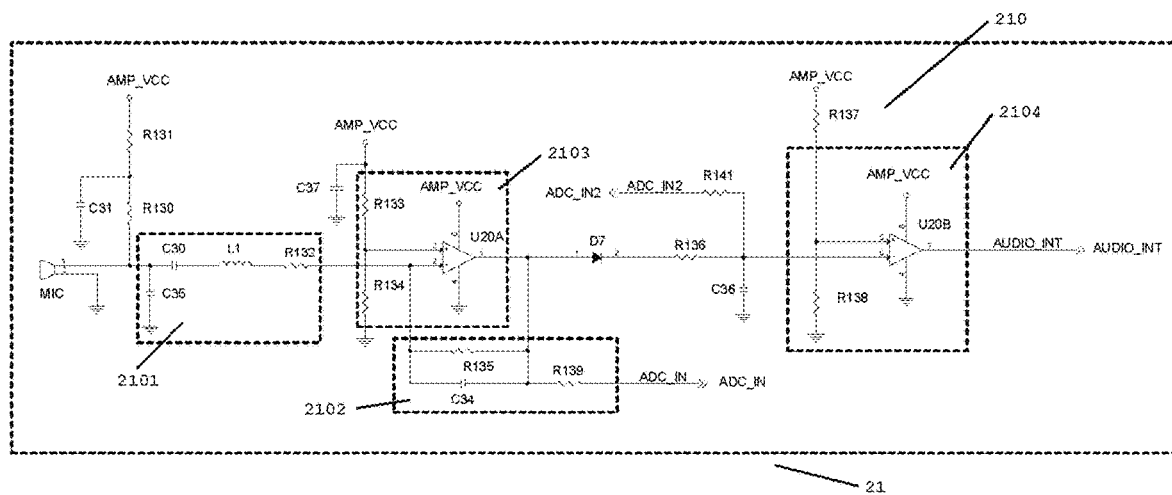
FIGS. 4A-B illustrate a circuit principle schematic diagram of a snore collecting circuit 21 of the working module 2 of the preferred embodiment.
Figure 4B:
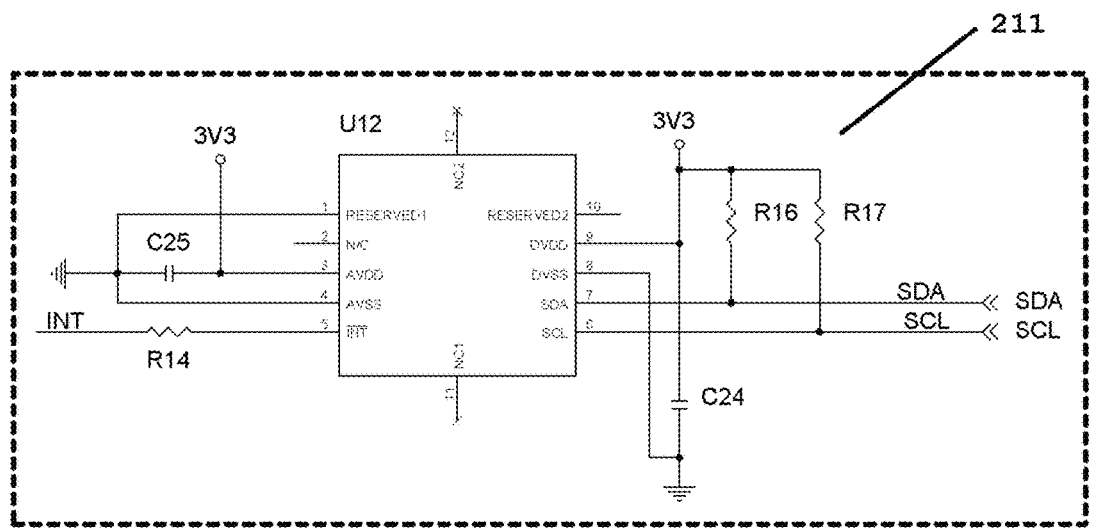

Please refer to FIG. 4, the snore collecting circuit 21 comprises a sound collecting circuit 210 taking the microphone as a core thereof, and a vibration collecting circuit 211 taking the vibration sensor as a core thereof; the sound collecting circuit 210 comprises a first low-frequency filter circuit 2101, a second low-frequency filter circuit 2102 and a first calculating and amplifying circuit 2103; the microphone transforms a collected sound signal into an electric signal, and the electric signal is transmitted to the first low-frequency filter circuit 2101 to be filtered; the filtered electric signal is transmitted to the first calculating and amplifying circuit 2103 to be amplified; the amplified electric signal is further transmitted to the second low-frequency filter circuit 2102 to be further filtered, and the further filtered electric signal is transmitted to a control circuit 22; the vibration sensor is a triaxial accelerated speed sensor integrated circuit U12, the triaxial accelerated speed sensor integrated circuit U12 of the vibration collecting circuit 211 transforms a sensed vibration signal into an electric signal and transmits the electric signal to the control circuit 22. The control circuit 22 judges whether the sound signal and vibration signal received by it reach their respective threshold values or not, and further judges whether the user is in a snoring status or not; when a sound being higher than or equal to 60 dB occurs three times or more in one minute, and the received vibration reaches a preset threshold value, an occurrence of a snore is confirmed. In order to make a better effect, the sound collecting circuit 210 of this embodiment is further provided with a second calculating and amplifying circuit 2104, that is, the electric signal filtered by the second low-frequency filter circuit 2102 is not only transmitted to the control circuit 22 but also transmitted to the second calculating and amplifying circuit 2104 to be amplified, and the further amplified electric signal is transmitted to the control circuit 22 to be compared with a snore experience value stored in the control circuit 22, such that whether the user snores or not can be judged. The experience value is obtained by pre-recoding and analysis of the user's snores.

Figure 5:
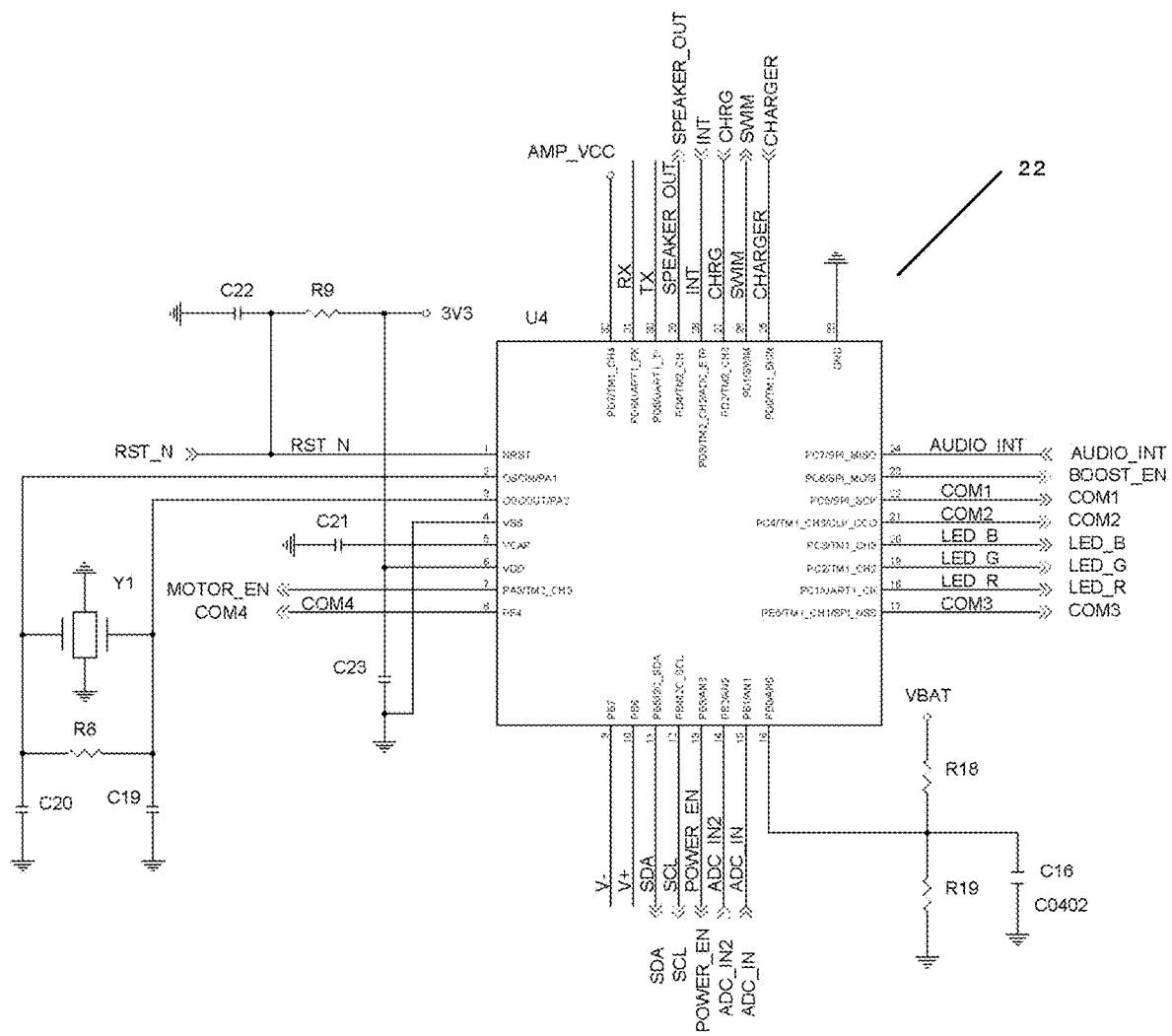
FIG. 5 illustrates a circuit principle schematic diagram of a control circuit 22 of the working module 2 of the preferred embodiment.

Please refer to FIG. 5, the control circuit 22 of this embodiment is constituted by taking a microprocessor integrated circuit U4 as a core thereof, the microprocessor integrated circuit U4 analyzes the sound signal and the vibration signal sent from the snore collecting circuit 21, when it has analyzed and confirmed that the user is snoring, the microprocessor integrated circuit U4 sends a warning signal to the warning circuit 23 for stimulating the snore maker. The warning modes include a sound warning, a vibration warning and an electrode stimulation warning. In this embodiment, the warning has four warning levels in an ascending order, one warning level is added when every three snores are detected, until the snores cease.

Figure 6:
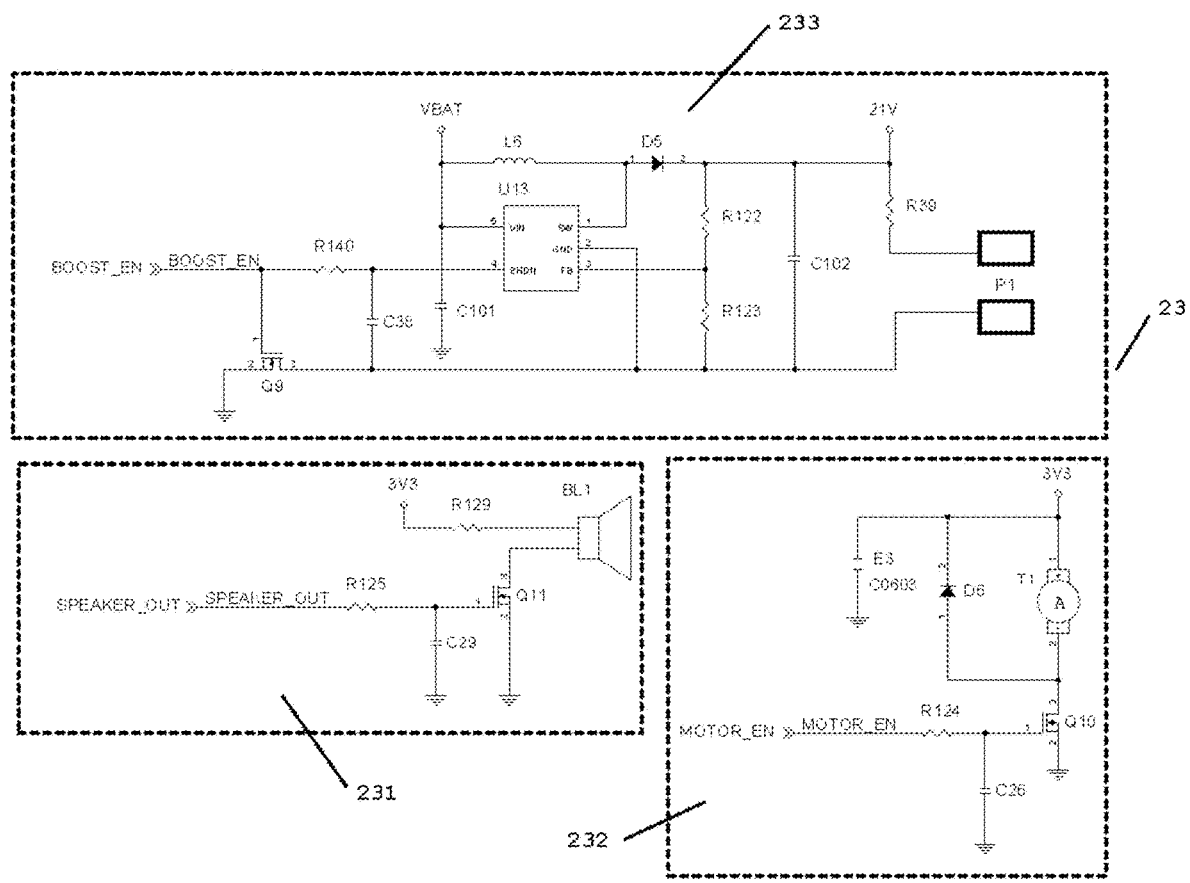
FIG. 6 illustrates a circuit principle schematic diagram of a warning circuit 23 of the working module 2 of the preferred embodiment.

Please refer to FIG. 6, in this embodiment, the warning circuit 23 comprises a sound stimulating circuit 231, a vibration stimulating circuit 232 and an electrode stimulating circuit 233, and the sound stimulating circuit 231, the vibration stimulating circuit 232, and the electrode stimulating circuit 233 are electrically connected to the control circuit 22 respectively. The control circuit 22 transmits a pulse signal, which triggers a loudspeaker BL 1 of the sound stimulating circuit 231 to generate a sound stimulation signal, or triggers a vibration electric motor of the vibration stimulating circuit 231 to generate a vibration stimulation signal, or triggers an electric shock piece P1 of the electrode stimulation circuit 231 to generate an electrode stimulation signal; the control circuit 22 changes a sound stimulation intensity, a vibration stimulation intensity, and/or an electrode stimulation intensity by adjusting a pulse width of the output pulse signal. In this embodiment, the stimulation signal modes for warning are switched according to an order of a sound stimulation mode, a vibration stimulation mode, and an electrode stimulation mode, thereby stimulating in sequence.

Figure 7:
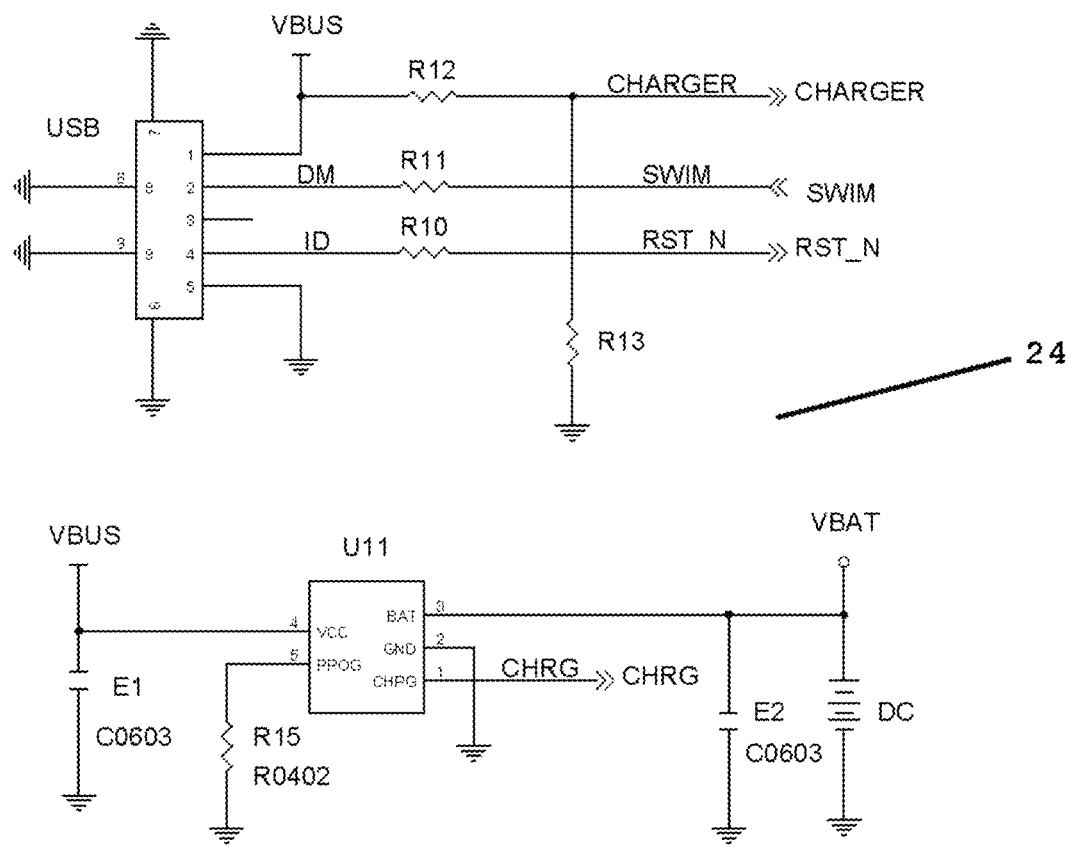
FIG. 7 illustrates a circuit principle schematic diagram of a power supply circuit 24 of the working module 2 of the preferred embodiment.

Please refer to FIG. 7, in this embodiment, the power supply circuit 24 comprises a Li-ion battery DC and a battery charging circuit 240, the battery charging circuit 240 is provided therein with a coupler which meets an USB standard, an external power supply can provide electric power to the battery charging circuit through the coupler so as to charge the Li-ion battery DC. Besides, the coupler meeting with the USB standard is also electrically connected to the control circuit 22, and works as a data exchange interface for the external.

Figure 8:
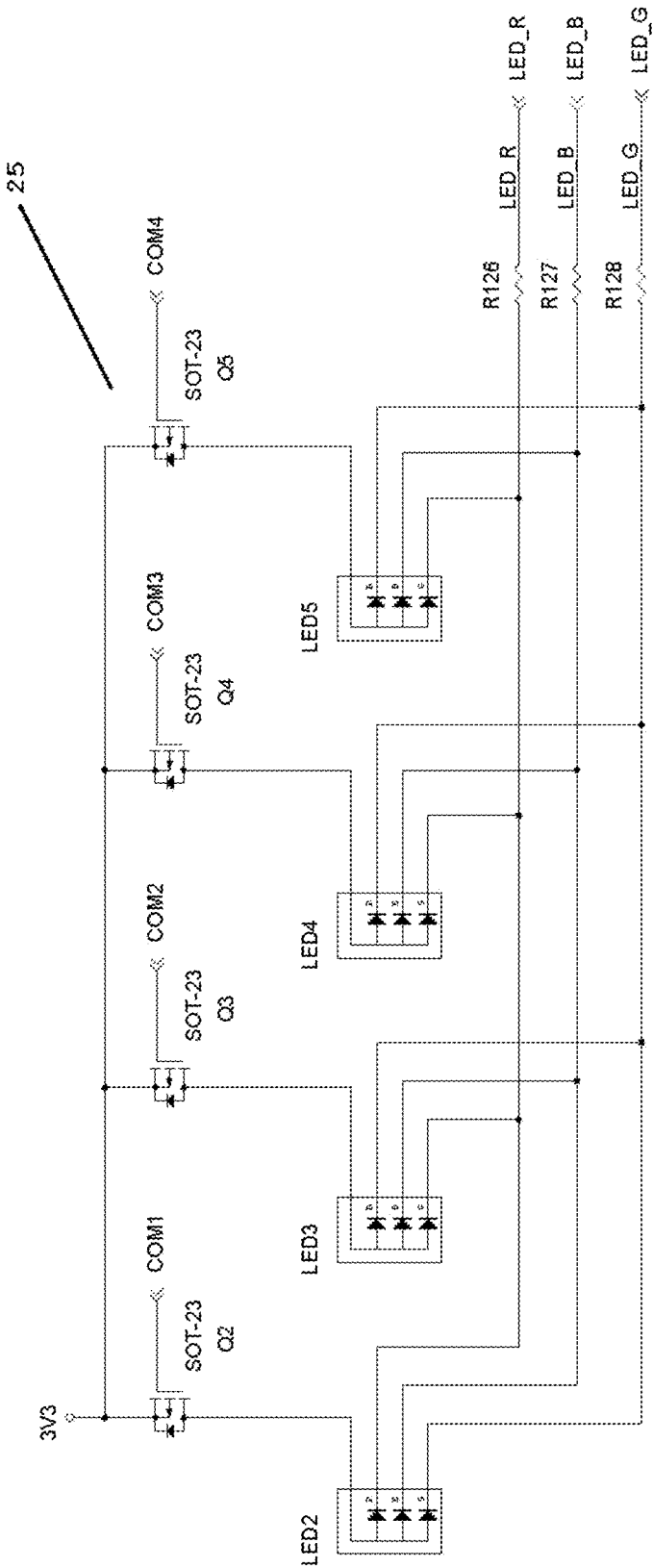
FIG. 8 illustrates a circuit principle schematic diagram of a status indicating circuit 25 of the working module 2 of the preferred embodiment.

Please refer to FIG. 8, in this embodiment, the working module 2 is further provided with a working condition displaying circuit 25, the working condition displaying circuit 25 is composed of a plurality of diodes and is configured for displaying various working conditions of the electronic snore-ceasing device.

Figure 9:
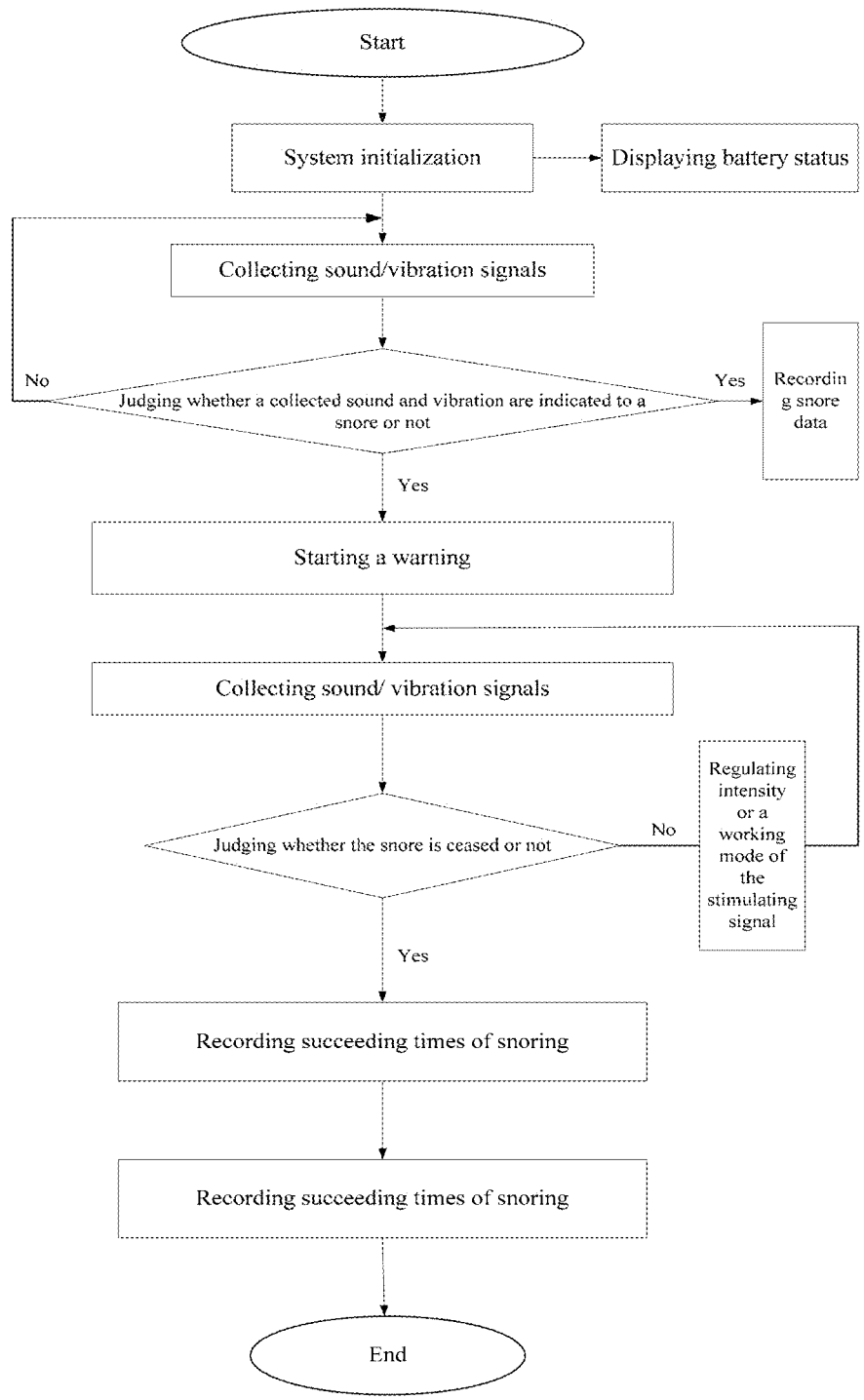
FIG. 9 illustrates a working flow chart of the electronic snore-ceasing device of the preferred embodiment.

Please refer to FIG. 9, a work flow of the electronic snore-ceasing device is introduced in the following:

step A. the working module 2 collects sound signals and head vibration signals generated by the user in sleep;

step B. when the working module 2 determines that a collected sound signal is greater than or equal to a sound threshold value, and a collected vibration signal is greater than or equal to a vibration threshold value, one of the sound stimulation mode, the vibration stimulation mode, and the electrode stimulation mode that does not wake the user up in sleep is generated and works for stimulating the user through the ear plug 12; meanwhile, the number of the snore, snore data, and/or vibration data are recorded for one time.

step C. the working module 2 collects the sound signals and the head vibration signals generated by the user in sleep, when it is determined that a collected sound signal is greater than or equal to the sound threshold value, and a collected vibration signal is greater than or equal to the vibration threshold value, one warning level of the original stimulation signal mode is added, or the original stimulation signal mode is changed; when it is determined that the collected sound signal is smaller than the preset sound threshold value, or the collected vibration signal is smaller than the vibration threshold value, returning back to step A, and the number of snore is recorded for one time.

In this embodiment, the main components for implementing aforesaid circuits are listed in the following table:

| Number | Label in the Circuit Diagram | Name of the Component | Specification and Type |
|---|---|---|---|
| 1 | BAT 1 | Li-ion battery | Gz031040 |
| 2 | P1 | Electric shock piece | |
| 4 | LS1 | Loudspeaker | 1306-1 |
| 5 | T1 | Vibration Motor | 3.3 V(JS1027W12 8-LW20E) |
| 6 | MIC | Microphone | -42 DB(zts6011) |
| 7 | U4 | Microprocessor integrated circuit | STM8S103K3 |
| 8 | U11 | Li-ion battery charging integrated circuit | Beiling BL4054_4.2 |
| 9 | U12 | Triaxial accelerated speed integrated circuit | MA7660FC |
| 10 | U13 | Synchronous direct current step-down transformer with the function of pulse-width modulation output | AX5510 |
| 11 | U20A, U20B | Amplifier | Shengbangwei SGM358 |

In use, the electronic snore-ceasing device of this embodiment is placed inside the ear of the user; the position of the snore collecting circuit 21 is very close to a human snore sound source, that is, a mouth cavity and/or a nasal cavity of the human, and thus is able to collect sounds generated by the human in sleep accurately. In combination with an application of our advanced digital voice mode recognition technology, real-time detections performed by the sound collecting circuit and the vibration collecting circuit taking the triaxial accelerate speed sensor as the core thereof provide a base for implementing stimulation and intervention, and further provides a reliable evidence for detecting a stimulation effect. When a patient's snore is accurately judged, the control circuit 22 sends a stimulation signal for controlling the snore mode, which drives the processing parts to apply stimulations with different intensities to the patient; the stimulations are recorded, and the snore-ceasing effect is collected by the microphone and the sensors and fed back, until the patient recovers a normal sleep condition and stops snoring.

When the technical solution of the present application is adopted, times of snores generated by the user and intensities and density of the snores can be recorded and serve as references for a doctor to diagnose a snore symptom of the patient, such that more accurate and scientific references for confirming a treatment protocol for the snore patient can be provided.

The invention claimed is:

1. An electronic snore-ceasing device, comprising a snore-ceasing device body and a working module received in the snore-ceasing device body, wherein:
   the body comprises an ear-hook that is suitable to be hung on an auricle of a user, and an ear plug that is suitable to be placed inside an earhole of the user, the ear-hook and the ear plug are jointed together; the working module is placed inside an inner cavity formed by the ear-hook and the ear plug;
   the working module comprises a snore collecting circuit, a control circuit with a Micro Control Unit (MCU) as a core thereof, a warning circuit, and a power supply circuit; the snore collecting circuit and the warning circuit are electrically connected to the control circuit respectively, the power supply circuit provides low-voltage direct current electric power for the snore-ceasing circuit, the control circuit and the warning circuit respectively; the snore collecting circuit processes a sound signal and a vibration signal made by the user in sleep and collected by a microphone and a vibration sensor thereof, and transmits the processed sound signal and the vibration signal respectively to the control circuit; when the control circuit judges that the received sound signal and the vibration signal reach their respective threshold values, the control circuit sends a control signal to the warning circuit positioned inside the ear plug, such that the warning circuit is controlled to generate a sound stimulation signal or a vibration stimulation signal or an electrode stimulation signal that does not wake the user up to suppress snores.

2. The electronic snore-ceasing device according to claim 1, further comprising:
   a snore collecting tube having a first end and a second end, the first end of the snore collecting tube is connected to the ear plug, and the second end of the snore collecting tube is directed to a mouth and a nose of the user, the microphone is positioned inside the snore collecting tube.

3. The electronic snore-ceasing device according to claim 1, wherein:
   the snore collecting circuit comprises a sound collecting circuit taking the microphone as a core thereof, and a vibration collecting circuit taking the vibration sensor as a core thereof;
   the sound collecting circuit comprises a first low-frequency filter circuit, a second low-frequency filter circuit and a first calculating and amplifying circuit; the microphone is configured for transforming a collected sound signal into an electric signal, wherein the electric signal to the first low-frequency filter circuit to be filtered, then the filtered electric signal is transmitted to the first calculating and amplifying circuit to be amplified, the amplified electric signal is transmitted to the second low-frequency filter circuit to be further filtered, and finally the further filtered electric signal is transmitted to the control circuit;
   the vibration sensor is a triaxial accelerated speed sensor with an integrated circuit (U12), the integrated circuit (U12) of the vibration collecting circuit transforms sensed vibration signals into transformed electric signals and transmits the transformed electric signals to the control circuit.

4. The electronic snore-ceasing device according to claim 3, wherein:
the sound collecting circuit further comprises a second calculating and amplifying circuit, the electric signal further filtered by the second low-frequency filter circuit is not only transmitted to the control circuit but also transmitted to the second calculating and amplifying circuit to be further amplified, and the further amplified electric signal is transmitted to the control circuit.

5. The electronic snore-ceasing device according to claim 1, wherein:
the warning circuit comprises a sound stimulating circuit, a vibration stimulating circuit and an electrode stimulating circuit, the sound stimulating circuit, the vibration stimulating circuit and the electrode stimulating circuit are respectively electrically connected to the control circuit; the control circuit outputs a pulse signal, which activates a loudspeaker (BL1) of the sound stimulating circuit to generate a sound stimulation signal, or activates a vibration electric motor (T1) of the vibration stimulating circuit to generate a vibration signal, or activates an electric shock piece (P1) of the electric stimulating circuit to generate an electrode stimulation signal.

6. A snore-ceasing method of an electric snore-ceasing device, comprising an electric snore-ceasing device body and a working module received in the electric snore-ceasing device body, the electric snore-ceasing device body comprises an ear-hook that is suitable to be hung on an auricle of a user, and an ear plug that is suitable to be placed inside an earhole of the user; the snore-ceasing method comprising:
step A) using the working module to collect sounds and head vibrations generated by the user in sleep;
step B) when the working module judges that a collected sound is greater than or equal to a sound threshold value, and a collected vibration is greater than or equal to a vibration threshold value, generating one of a signal stimulation signal mode, a vibration stimulation signal mode, and an electrode stimulation signal mode that does not wake up the user and stimulates the user through the ear plug;
step C) using the working module to collect the sounds and the head vibrations generated by the user in sleep again, when it is judged that a collected sound signal is still greater than or equal to the sound threshold value, and a collected vibration signal still reaches the vibration threshold value, enhancing an intensity of an original stimulation signal mode, or switching to the vibration or electrode stimulation signal mode; when it is judged that the collected sound signal is smaller than the sound threshold value, or the collected vibration signal is less than the vibration threshold value, returning back to the step A.

7. The snore-ceasing method according to claim 6, further comprising:
when the working module determines that the collected sound is greater than or equal to the sound threshold value, and the collected vibration is greater than or equal to the vibration threshold value, recording a number of the snore, snore data and/or vibration data for one time.

8. The snore-ceasing method according to claim 6, further comprising:
when the working module determines that the collected sound is smaller than the sound threshold value, or the collected vibration is smaller than the vibration threshold value, recording a number of the snore-ceasing operation for one time.

9. The snore-ceasing method according to claim 6, further comprising:
the sound threshold value is set as sounds with a volume of 60 dB or more occurs for three or more times in one minute, or set as an experience value obtained by pre-recording and analyzing the user's snores.

10. The snore-ceasing method according to claim 6, wherein:
the working module comprises a snore collecting circuit, a control circuit with a Micro Control Unit (MCU) as a core thereof, a warning circuit, and a power supply circuit; the snore collecting circuit and the warning circuit are electrically connected to the control circuit respectively, the power supply circuit provides electric power respectively for the snore-ceasing circuit, the control circuit and the warning circuit respectively; the snore collecting circuit collects sounds and head vibrations generated by the user in sleep by using a microphone and a vibration sensor thereof.

11. The snore-ceasing method according to claim 10, wherein:
the snore collecting circuit comprises a sound collecting circuit taking the microphone as a core thereof, and a vibration collecting circuit taking the vibration sensor as a core thereof;
the sound collecting circuit comprises a first low-frequency filter circuit, a second low-frequency filter circuit and a first calculating and amplifying circuit; by using the microphone, transforming a collected sound signal into an electric signal, transmitting the electric signal to the first low-frequency filter circuit to be filtered, and then transmitting the filtered electric signal to the first calculating and amplifying circuit to be amplified, and transmitting the amplified electric signal to the second low-frequency filter circuit to be further filtered, and transmitting the further filtered electric signals to the control circuit;
the vibration sensor is a triaxial accelerated speed sensor with an integrated circuit (U12), by using the integrated circuit (U12) of the vibration collecting circuit, transforming the sensed vibration signal into the electric signal and further transmitting the electric signal to the control circuit.

12. The snore-ceasing method according to claim 6, further comprising:
setting a snore collecting tube having a first end and a second end, the first end of the snore collecting tube is communicated with the ear plug, the second end of the snore collecting tube is directed to a mouth and/or a nose of the user, a microphone of the working module is placed inside the snore collecting tube to collect the sounds generated by the user in sleep in a close proximity.

* * * * *